U S010391046B2

(12) United States Patent
Hartnett et al.

(10) Patent No.: US 10,391,046 B2
(45) Date of Patent: Aug. 27, 2019

(54) PERSONAL CARE COMPOSITIONS

(71) Applicant: COLGATE-PALMOLIVE COMPANY, New York, NY (US)

(72) Inventors: Donna Ann Hartnett, Belle Mead, NJ (US); Cheryl Kozubal, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/393,540

(22) Filed: Dec. 29, 2016

(65) Prior Publication Data

US 2017/0239155 A1    Aug. 24, 2017

Related U.S. Application Data

(60) Provisional application No. 62/297,721, filed on Feb. 19, 2016.

(51) Int. Cl.
| | |
|---|---|
| *A61K 8/04* | (2006.01) |
| *A61K 8/20* | (2006.01) |
| *A61K 8/27* | (2006.01) |
| *A61K 8/34* | (2006.01) |
| *A61K 8/37* | (2006.01) |
| *A61K 8/44* | (2006.01) |
| *A61K 8/46* | (2006.01) |
| *A61K 8/49* | (2006.01) |
| *A61K 8/60* | (2006.01) |
| *A61K 8/64* | (2006.01) |
| *A61K 8/67* | (2006.01) |
| *A61K 8/73* | (2006.01) |
| *A61K 8/86* | (2006.01) |
| *A61K 8/88* | (2006.01) |
| *A61Q 5/00* | (2006.01) |
| *A61Q 5/02* | (2006.01) |
| *A61Q 5/12* | (2006.01) |
| *A61K 8/365* | (2006.01) |
| *A61K 8/368* | (2006.01) |
| *A61Q 19/10* | (2006.01) |

(52) U.S. Cl.
CPC .............. *A61K 8/375* (2013.01); *A61K 8/042* (2013.01); *A61K 8/20* (2013.01); *A61K 8/27* (2013.01); *A61K 8/34* (2013.01); *A61K 8/365* (2013.01); *A61K 8/368* (2013.01); *A61K 8/44* (2013.01); *A61K 8/442* (2013.01); *A61K 8/463* (2013.01); *A61K 8/4913* (2013.01); *A61K 8/4926* (2013.01); *A61K 8/60* (2013.01); *A61K 8/604* (2013.01); *A61K 8/64* (2013.01); *A61K 8/67* (2013.01); *A61K 8/678* (2013.01); *A61K 8/731* (2013.01); *A61K 8/86* (2013.01); *A61K 8/88* (2013.01); *A61Q 5/006* (2013.01); *A61Q 5/02* (2013.01); *A61Q 5/12* (2013.01); *A61Q 19/10* (2013.01); *A61K 2800/26* (2013.01); *A61K 2800/48* (2013.01); *A61K 2800/524* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 4,938,953 A | 7/1990 | Pena et al. | |
| 5,632,978 A | 5/1997 | Moore et al. | |
| 5,866,110 A | 2/1999 | Moore et al. | |
| 6,265,368 B1 | 7/2001 | Aronson et al. | |
| 6,361,768 B1 | 3/2002 | Galleguillos et al. | |
| 6,776,995 B1 | 8/2004 | Revivo | |
| 7,008,618 B1 | 3/2006 | Hessefort et al. | |
| 7,238,652 B2 | 7/2007 | Carnali et al. | |
| 2011/0104085 A1* | 5/2011 | Klug ................... A61K 8/898 424/59 |
| 2013/0115185 A1* | 5/2013 | Tamareselvy ......... A61K 8/025 424/70.16 |
| 2013/0253057 A1 | 9/2013 | Wei et al. | |
| 2014/0023606 A1 | 1/2014 | Scheunemann et al. | |
| 2014/0349902 A1 | 11/2014 | Allef et al. | |
| 2015/0315123 A1 | 11/2015 | Schuch et al. | |

FOREIGN PATENT DOCUMENTS

| | | |
|---|---|---|
| EP | 1250906 | 10/2002 |
| EP | 1932512 | 6/2008 |
| EP | 2314274 | 4/2011 |
| EP | 2591027 | 9/2015 |
| WO | WO 2007/127987 | 11/2007 |
| WO | WO 2012/142407 | 10/2012 |
| WO | WO 2016/071187 | 5/2016 |
| WO | WO 2016/077329 | 5/2016 |
| WO | WO 2016/101207 | 6/2016 |
| WO | WO 2017/11 6458 | 7/2017 |

OTHER PUBLICATIONS

International Search Report and Written Opinion in International Application No. PCT/US2016/069098, dated Mar. 20, 2017.

* cited by examiner

*Primary Examiner* — Aradhana Sasan

(57) ABSTRACT

The present disclosure provides personal care compositions comprising a surfactant system that includes an anionic surfactant, a zwitterionic or amphoteric surfactant and optionally a non-ionic surfactant; a preservative system; a pH modifier; optionally a moisturizer or a skin conditioner or both a moisturizer and a skin conditioner; and a viscosity adjusting system, wherein the viscosity adjusting system comprises glyceryl oleate and at least one additional viscosity adjusting agent. Use of the viscosity adjusting system can achieve viscosity levels that would otherwise not be possible by either agent alone, and allows for higher maximum viscosity levels while at the same time providing an emolliency to the formulation.

31 Claims, No Drawings

PERSONAL CARE COMPOSITIONS

BACKGROUND

In recent years, foaming emulsions, particularly for shower gel products, facial washes and shampoos have become increasingly popular in various areas of the world. These compositions can provide skin or hair cleansing and caring in one application. In order for such compositions to be effective, one should have a physically stable composition with high foaming characteristics but which remains mild to the skin and provide an appropriate skin feel and conditioning effect during and after use. To meet the various demands and requirements for such compositions, many of the available products include a one or more thickening agents to achieve the desired viscosities.

Thickening of surfactant solutions is typically achieved with sodium chloride or known thickening agents that provide the singular thickening benefit. Due to many factors such as cost and the desire for more simple formulations, it is advantageous to utilize multi-functional ingredients that can provide multiple benefits.

BRIEF SUMMARY

In some embodiments, the present disclosure provides personal care compositions including shampoos, shower gels and face washes, that comprise a viscosity adjusting system that includes glyceryl oleate and at least one additional thickening agent.

It has been discovered that glyceryl oleate, which is a known emollient and emulsifier, can also act as a thickening or viscosity adjusting agent, and enhance the thickening effects of other thickening agents, for example and not limitation inorganic salts and modified sugar thickeners. The use of glyceryl oleate as a thickening agent, in particular in combination with another thickening agent, can achieve viscosity levels that would otherwise not be possible by either agent alone, or be predicted by their individual contribution to the viscosity increase. Thus, the addition of glyceryl oleate as a thickener allows for higher maximum viscosity levels while at the same time providing an emolliency to the formulation.

DETAILED DESCRIPTION

Unless otherwise specified, all percentages and amounts expressed herein and elsewhere in the specification should be understood to refer to percentages by weight. The weight percentages as expressed herein are understood to refer to the percentage by weight of active components based on the total weight of a personal care composition as described herein. For example, for if 11.7 wt % of a 70% surfactant solution is employed in a given formulation as described herein, the % surfactant would be 8.19 wt % of the composition (i.e., the % of the active).

The term "about," when used in reference to a range of values, should be understood to refer to either value in the range, or to both values in the range. As used throughout, ranges are used as shorthand for describing each and every value that is within the range. Any value within the range can be selected as the terminus of the range.

The present disclosure provides personal care compositions comprising a viscosity adjusting system that comprises glyceryl oleate and at least one additional viscosity adjusting agent. Preferably, the composition comprises water as a carrier. The compositions may comprise a surfactant system having an anionic surfactant and a zwitterionic surfactant, and optionally a nonionic surfactant. The composition may further comprise a preservative, a pH modifier, and optionally a moisturizer or a skin conditioner, or both a moisturizer and a skin conditioner.

In one exemplary embodiment, the present disclosure provides personal care composition (Composition 1) comprising:

a surfactant system consisting essentially of:
an anionic surfactant;
a zwitterionic or amphoteric surfactant; and
optionally a non-ionic surfactant;
a preservative system;
a pH modifier;
optionally a moisturizer or a skin conditioner or both a moisturizer and a skin conditioner; and
a viscosity adjusting system,
wherein the viscosity adjusting system comprises glyceryl oleate and at least one additional viscosity adjusting agent.

The present disclosure provides additional exemplary embodiments, including:

1.1 Composition 1, wherein the viscosity adjusting system consists essentially of glyceryl oleate and at least one additional viscosity adjusting agent selected from Glucamate™ LT, lipid thickeners such as cetyl alcohol, stearyl alcohol, isopropyl palmitate, isopropyl myristate, a polymer, carnauba wax, and stearic acid; natural thickeners such as hydroxyethylcellulose, guar gum, locust bean gum, xanthan gum, and gelatin; mineral thickeners such as silica, bentonite, and magnesium aluminum silicate; and synthetic thickeners such as carbomer thickeners; and inorganic salts and other electrolytes such as sodium chloride and other mono-, di- and trivalent salts, and a hydrotrope.

1.2 Composition 1 or 1.1, wherein the viscosity adjusting system consists essentially of glyceryl oleate and one additional viscosity adjusting agent.

1.3 Composition 1 or 1.1-1.2, wherein the viscosity adjusting system consists essentially of glyceryl oleate and Glucamate™ LT.

1.4 Composition 1 or 1.1-1.2, wherein the viscosity adjusting system consists essentially of glyceryl oleate and Glucamate™ LT; wherein the glyceryl oleate is present in an amount of from 0.2-0.8% by weight of the composition; and the Glucamate™ LT is present in an amount of from 0.1-2.5% by weight of the composition.

1.5 Composition 1 or 1.1-1.4, wherein the surfactant system consists essentially of an anionic surfactant and an amphoteric surfactant, and is free of other surfactants.

1.6 Composition 1 or 1.1-1.5, wherein the weight ratio of anionic surfactant to amphoteric surfactant is from about 1:1 to about 4:1, about 1.5:1 to about 3.5:1, about 2:1 to about 3:1, or about 2.5:1 by weight, based on the active weight of the surfactant.

1.7 Composition 1 or 1.1-1.6, wherein the anionic surfactant is an alkyl ether sulfate, for example a linear $C_8$-$C_{18}$ alkyl ether sulfate, for example selected from sodium laureth sulfate, sodium lauryl sulfate, and ammonium lauryl sulfate, for example sodium laureth sulfate.

1.8 Composition 1 or 1.1-1.7, wherein the amphoteric surfactant is a N,N-disubstituted glycine derivative; for example a N-(2-aminoethyl)-N-(2-hydroxyethyl) glycine derivative; for example a cocoamphoacetate salt, for example sodium cocoamphoacetate. 1.9 Composition 1 or 1.1-1.8, wherein the surfactant system comprises about 5 wt % to about 15 wt %, about 7 wt % to about 13 wt %, about 8 wt % to about 12 wt %, about 9-11 wt %, or about 10-11 wt %, or about 10 wt % of the composition, or about 11 wt % of the composition.

1.10 Composition 1 or 1.1-1.9, wherein the pH modifier is selected from lactic acid, sodium lactate, citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, and a combination of two or more thereof.

1.11 Composition 1 or 1.1-1.10, wherein the preservative system comprises one ore more preservatives selected from sodium benzoate, sodium salicylate, benzalkonium chloride, benzethonium chloride, 5-bromo-5-nitro-1,3-dioxane, 2-bromo-2-nitropropane-1,3-diol, alkyl trimethyl ammonium bromide, N-(hydroxymethyl)-N-(1,3-dihydroxy methyl-2,5-dioxo-4-imidaxolidinyl-N-(hydroxy methyl) urea, 1-3-dimethyol-5,5-dimethyl hydantoin, iodopropynyl butyl carbamate, butyl paraben, ethyl paraben, methyl paraben, propyl paraben, methyl isothiazolinone, methyl-chloroisothiazoline, phenoxyethanol, tris-hydroxyethyl-hexahydrotriazine, methylisothiazolinone, 5-chloro-2-methyl-4-isothiazolin-3-one, 1,2-dibromo-2,4-dicyanobutane, 1-(3-chloroalkyl)-3,5,7-triaza-azoniaadamantane chloride, organic acids, or combinations thereof.

1.12 Composition 1 or 1.1-1.11, wherein the preservative system comprises at least two preservatives.

1.13 Composition 1 or 1.1-1.12, wherein the preservative system comprises phenoxyethanol and sodium benzoate in a weight ratio of from 0.8:1 to 1.2:1.

1.14 Composition 1 or 1.1-1.13, wherein the composition comprises a moisturizer and a conditioner.

1.15 Composition 1.14, wherein the moisturizer and conditioner are selected from long chain fatty acids; liquid water-soluble polyols; glycerin; propylene glycol; sorbitol; polyethylene glycol; ethoxylated/propoxylated ethers of methyl glucose (eg., methyl gluceth-20) and ethoxylated/propoxylated ethers of lanolin alcohol (e.g., Solulan-75); coco and tallow fatty acids; nonoclusive liquid water soluble polyols; essential amino acids; sodium pyrrolidone carboxylic acid (or sodium dl-pyrrolidone carboxylate); urea; L-proline; guanidine; pyrrolidone; hexadecyl, myristyl, isodecyl or isopropyl esters of adipic, lactic, oleic, stearic, isostearic, myristic or linoleic acids and corresponding alcohol esters such as sodium isostearoyl-2 lactylate, sodium capryl lactylate; aloe vera gel and acetamide MEA; and film forming and conditioning polymers such as polyquaternium polymers; for example Polyquaternium 7 and Polyquaternium 10.

1.16 Composition 1 or 1.1-1.15, wherein the personal care composition is a shampoo composition.

1.17 Composition 1.16, further comprising an anti-dandruff active; for example selected from piroctone olamine, zinc omadine, climbazole, pyridinethione salts, azoles, selenium sulfide, particulate sulfur, keratolytic agents, and mixtures thereof.

1.18 Composition 1.16 or 1.17, further comprising one or more optional ingredients selected from fragrances, vitamins, extracts, proteins, antioxidants, pearlizers, opacifiers and a combination of two or more thereof.

1.19 Any of Compositions 1.16-1.18, comprising added water in an amount of from 65% to 75% by weight of the composition, for example from 68% to 72% by weight of the composition.

1.20 Any of Compositions 1 or 1.1-1.19, wherein the pH of the composition is from 4-5, for example, from 4.2-4.8.

In a second exemplary embodiment, the invention includes a personal care composition (Composition 2) comprising Composition 1 or 1.1 described above, wherein the viscosity adjusting system consists essentially of glyceryl oleate and an inorganic salt.

The present disclosure provides additional exemplary embodiments, including:

2.1 Composition 2, wherein the viscosity adjusting system consists essentially of glyceryl oleate and sodium chloride; wherein the glyceryl oleate is present in an amount of from 0.1-1% by weight of the composition, for example from about 0.3-0.7% by weight of the composition for example about 0.5% by weight of the composition; and the sodium chloride is present in an amount of from 0.1-1.5% by weight of the composition; for example from 0.3-0.8%, for example from about 0.4-0.5% by weight of the composition.

2.2 Composition 2 or 2.1, wherein the surfactant system consists essentially of an anionic surfactant, a zwitterionic surfactant, and a nonionic surfactant.

2.3 Any of compositions 2 or 2.1-2.2, wherein the weight ratio of anionic surfactant to zwitterionic surfactant to non-ionic surfactant is from about (5.5-7.5):(0.5-1.5):(0.8-1.2); for example about (6-7):(1-1.3):(0.9-1.1); for example about 6.5:1.1:1 by weight, based on the active weight of the surfactant.

2.4 Any of Compositions 2 or 2.1-2.3, wherein the anionic surfactant is an alkyl ether sulfate, for example a linear $C_8$-$C_{18}$ alkyl ether sulfate, for example selected from sodium laureth sulfate, sodium lauryl sulfate, and ammonium lauryl sulfate, for example sodium laureth sulfate.

2.5 Any of Compositions 2 or 2.1-2.4, wherein the zwitterionic surfactant is a quaternary ammonium carboxylate betaine.

2.6 Any of Compositions 2 or 2.1-2.5, wherein the zwitterionic surfactant is cocoamidopropyl betaine.

2.7 Any of Compositions 2 or 2.1-2.6, wherein the nonionic surfactant is selected from ethoxylated aliphatic alcohols, alkyl glucosides such as coco glucoside, polyoxyethylene surfactants, carboxylic esters, polyethylene glycol esters, anhydrosorbitol ester and it's ethoxylated derivatives, glycol esters of fatty acids, carboxylic amides, monoalkanolamine condensates and polyoxyethylene fatty acid amides; for example coco-glucoside.

2.8 Any of Compositions 2 or 2.1-2.7, wherein the surfactant system comprises about 5 wt % to about 15 wt %, about 7 wt % to about 13 wt %, about 8 wt % to about 12 wt %, about 9-11 wt %, or about 10-11 wt %, or about 10 wt % of the composition, or about 11 wt % of the composition.

2.9 Any of Compositions 2 or 2.1-2.8, wherein the pH modifier is selected from lactic acid, sodium lactate, citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, and a combination of two or more thereof; for example lactic acid and sodium lactate.

2.10 Any of Compositions 2 or 2.1-2.9, wherein the preservative system comprises one ore more preservatives selected from sodium benzoate, sodium salicylate, benzalkonium chloride, benzethonium chloride, 5-bromo-5-nitro-1,3-dioxane, 2-bromo-2-nitropropane-1,3-diol, alkyl trimethyl ammonium bromide, N-(hydroxymethyl)-N-(1,3-dihydroxy methyl-2,5-dioxo-4-imidaxolidinyl-N-(hydroxy methyl)urea, 1-3-dimethyol-5,5-dimethyl hydantoin, iodopropynyl butyl carbamate, butyl paraben, ethyl paraben, methyl paraben, propyl paraben, methyl isothiazolinone, methyl-chloroisothiazoline, phenoxyethanol, tris-hydroxyethyl-hexahydrotriazine, methylisothiazolinone, 5-chloro-2-methyl-4-isothiazolin-3-one, 1,2-dibromo-2,4-dicyanobutane, 1-(3-chloroalkyl)-3,5,7-triaza-azoniaadamantane chloride, organic acids, or combinations thereof.

2.11 Any of Compositions 2 or 2.1-2.10, wherein the preservative system comprises at least two preservatives.

2.12 Any of Compositions 2 or 2.1-2.11, wherein the preservative system comprises sodium benzoate and sodium salicylate in a weight ratio of from 1:1 to 2:1, for example from 1:1 to 1.5:1; for example from 1.3:1 to 1.4:1.

2.13 Any of Compositions 2 or 2.1-2.12, wherein the personal care composition is a shower gel composition.

2.14 Composition 2.13, further comprising a zinc salt skin flora regulator active; for example selected from zinc sulfate, zinc oxide, or zinc lactate, preferably zinc sulfate, and mixtures thereof.

2.15 Composition 2.13 or 2.14, further comprising caprylyl glycol active; for example in an amount of from about 0.01-0.25%, for example 0.05-0.15%, for example about 0.1% by weight of the shower gel composition.

2.16 Any of Compositions 2.13-2.15, further comprising a humectant selected from glycerin, lactic acid, propylene glycol, sodium PCA, sorbitol, and mixtures thereof, preferably glycerin and/or lactic acid; for example in an amount of from about 1-10% by weight of the composition, for example from about 5-10%, for example from about 6%-8% by weight of the composition.

2.17 Any of Compositions 2.13-2.16, further comprising one or more optional ingredients selected from fragrances, vitamins, extracts, proteins, antioxidants, pearlizers, opacifiers and a combination of two or more thereof.

2.18 Any of Compositions 2 and 2.1-2.17, comprising added water in an amount of from 65% to 75% by weight of the composition, for example from 68% to 72% by weight of the composition.

2.19 Any of Compositions 2 or 2.1-1.18, wherein the pH of the composition is from 4-5, for example, from 4.2-4.8.

In a third exemplary embodiment, the invention includes a personal care composition (Composition 3) comprising Composition 1 or 1.1 described above, wherein the viscosity adjusting system consists essentially of glyceryl oleate, an inorganic salt, and optionally one additional viscosity adjusting agent.

The present disclosure provides additional exemplary embodiments, including:

3.1 Composition 3, wherein the viscosity adjusting system consists essentially of glyceryl oleate, sodium chloride and optionally Glucamate™ LT.

3.2 Composition 3.1, wherein:
the glyceryl oleate is present in an amount of from 0.1-0.8% by weight of the composition, for example from 0.1-0.4% by weight of the composition, for example from 0.2-0.3% by weight of the composition;
the sodium chloride is present in an amount of from 0.1-1.25% by weight of the composition, for example from 0.3-0.8% by weight of the composition, for example from about 0.7-0.8% by weight of the composition, or from about 0.3-0.45% by weight of the composition; and
the Glucamate™ LT is optionally present in an amount of from about 0.1-0.8%, for example from about 0.2-0.6%, for example about 0.3-0.5%, for example about 0.4% by weight of the composition.

3.3 Composition 3.2, wherein:
the glyceryl oleate is present in an amount of from 0.2-0.3% by weight of the composition;
the sodium chloride is present in an amount of from about 0.7-0.8% by weight of the composition, or from about 0.3-0.45% by weight of the composition; and
the Glucamate™ LT is optionally present in an amount of from about 0.1-0.8%, for example from about 0.3-0.5% by weight of the composition.

3.4 Composition 3 or 3.1-3.3, wherein the surfactant system consists essentially of an anionic surfactant, a zwitterionic surfactant, and a nonionic surfactant.

3.5 Composition 3.4, wherein the weight ratio of anionic surfactant to zwitterionic surfactant to non-ionic surfactant is from about (4.5-7):(1-3):(0.8-1.2); for example about (5.5-6.5):(1-2):(0.9-1.1); for example about (5.6-6):(1.4-1.9):(1) by weight, based on the active weight of the surfactant.

3.6 Composition 3 or 3.1-3.5, wherein the anionic surfactant is an alkyl ether sulfate, for example a linear $C_8$-$C_{18}$ alkyl ether sulfate, for example selected from sodium laureth sulfate, sodium lauryl sulfate, and ammonium lauryl sulfate, for example sodium laureth sulfate.

3.7 Composition 3 or 3.1-3.6, wherein the zwitterionic surfactant is a quaternary ammonium carboxylate betaine; for example cocoamidopropyl betaine.

3.8 Composition 3 or 3.1-3.7, wherein the non-ionic surfactant is selected from ethoxylated aliphatic alcohols, alkyl glucosides such as coco glucoside, polyoxyethylene surfactants, carboxylic esters, polyethylene glycol esters, anhydrosorbitol ester and it's ethoxylated derivatives, glycol esters of fatty acids, carboxylic amides, monoalkanolamine condensates and polyoxyethylene fatty acid amides; for example coco-glucoside.

3.9 Composition 3 or 3.1-3.8, wherein the surfactant system comprises about 5 wt % to about 15 wt %, about 7 wt % to about 13 wt %, about 8 wt % to about 12 wt %, about 9-11 wt %, or about 10-11 wt %, or about 10 wt % of the composition, or about 11 wt % of the composition.

3.10 Composition 3 or 3.1-3.9, wherein the pH modifier is selected from lactic acid, sodium lactate, citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, and a combination of two or more thereof; for example lactic acid and sodium lactate.

3.11 Composition 3 or 3.1-3.10, wherein the preservative system comprises one ore more preservatives selected from sodium benzoate, sodium salicylate, benzalkonium chloride, benzethonium chloride, 5-bromo-5-nitro-1,3-dioxane, 2-bromo-2-nitropropane-1,3-diol, alkyl trimethyl ammonium bromide, N-(hydroxymethyl)-N-(1,3-dihydroxy methyl-2,5-dioxo-4-imidaxolidinyl-N-(hydroxy methyl) urea, 1-3-dimethyol-5,5-dimethyl hydantoin, iodopropynyl butyl carbamate, butyl paraben, ethyl paraben, methyl paraben, propyl paraben, methyl isothiazolinone, methyl-chloroisothiazoline, phenoxyethanol, tris-hydroxyethyl-hexahydrotriazine, methylisothiazolinone, 5-chloro-2-methyl-4-isothiazolin-3-one, 1,2-dibromo-2,4-dicyanobutane, 1-(3-chloroalkyl)-3,5,7-triaza-azoniaadamantane chloride, organic acids, or combinations thereof.

3.12 Composition 3 or 3.1-3.11, wherein the preservative system comprises at least two preservatives.

3.13 Composition 3 or 3.1-3.12, wherein the preservative system comprises sodium benzoate and sodium salicylate in a weight ratio of from 1:1 to 2:1, for example from 1:1 to 1.5:1; for example from 1.3:1 to 1.4:1.

3.14 Composition 3 or 3.1-3.13, wherein the personal care composition is a face wash composition.

3.15 Composition 3.14, further comprising a zinc salt skin flora regulator active; for example selected from zinc sulfate, zinc oxide, or zinc lactate, preferably zinc sulfate, and mixtures thereof.

3.16 Composition 3 or 3.1-3.15, further comprising a humectant selected from glycerin, lactic acid, propylene glycol, sodium PCA, sorbitol, and mixtures thereof, preferably glycerin and/or lactic acid; for example in an amount of from about 1-10% by weight of the composition, for example from about 5-10%, for example from about 6%-8% by weight of the composition, or for example from 1-3% by weight of the composition.

3.17 Composition 3 or 3.1-3.16, further comprising a conditioner.

3.18 Composition 3.17, wherein the conditioner is selected from long chain fatty acids; liquid water-soluble polyols; glycerin; propylene glycol; sorbitol; polyethylene glycol; ethoxylated/propoxylated ethers of methyl glucose (eg., methyl gluceth-20) and ethoxylated/-propoxylated ethers of lanolin alcohol (e.g., Solulan-75); coco and tallow fatty acids; nonoclusive liquid water soluble polyols; essential amino acids; sodium pyrrolidone carboxylic acid (or sodium dl-pyrrolidone carboxylate); urea; L-proline; guanidine; pyrrolidone; hexadecyl, myristyl, isodecyl or isopropyl esters of adipic, lactic, oleic, stearic, isostearic, myristic or linoleic acids and corresponding alcohol esters such as sodium isostearoyl-2 lactylate, sodium capryl lactylate; aloe vera gel and acetamide MEA; and film forming and conditioning polymers such as polyquaternium polymers; for example Polyquaternium 7 and Polyquaternium 10, for example Polyquaternium 7.

3.19 Composition 3 or 3.1-3.18, further comprising caprylyl glycol; for example in an amount of from about 0.01-0.25%, for example 0.05-0.15%, for example about 0.1% by weight of the shower gel composition.

3.20 Composition 3 or 3.1-3.19, further comprising one or more optional ingredients selected from fragrances, vitamins, extracts, proteins, antioxidants, pearlizers, opacifiers and a combination of two or more thereof.

3.21 Composition 3 or 3.1-3.20, comprising added water in an amount of from 65% to 75% by weight of the composition, for example from 68% to 72% by weight of the composition.

In a further exemplary embodiment, the invention includes a method (Method 1) of cleansing hair comprising the steps of providing a shampoo composition as described above (e.g., any of Composition 1 or 1.1-1.20); and applying the composition to the hair to provide a cleansing effect In a further exemplary embodiment, the invention includes a method (Method 2) of cleansing skin comprising the steps of providing a personal care cleansing composition as described above (e.g., any of Composition 2, or 2.1-2.19, or Composition 3, or 3.1-3.21); and applying the composition to the skin to provide a cleansing effect.

In some embodiments, the invention includes a method (Method 3) for preparing a personal care cleansing composition comprising combining an effective amount of a preservative, a pH modifier, and a viscosity adjusting system comprising glyceryl oleate and at least one additional viscosity adjusting agent, with a surfactant system comprising an anionic surfactant and a zwitterionic surfactant.

In a further exemplary embodiment, the invention includes a method (Method 4) of increasing viscosity of a shampoo composition comprising combining a shampoo formulation comprising one or more surfactants, a preservative, a pH modifier and a moisturizer, with a viscosity adjusting system comprising glyceryl oleate and at least one additional viscosity adjusting agent.

In a further exemplary embodiment, the invention includes a method (Method 5) of increasing viscosity of a shower gel composition comprising combining a shower gel formulation comprising one or more surfactants, a preservative, a pH modifier and optionally a moisturizer, with a viscosity adjusting system comprising glyceryl oleate and at least one additional viscosity adjusting agent.

In a further exemplary embodiment, the invention includes a method (Method 6) of increasing viscosity of a face wash composition comprising combining a face wash formulation comprising one or more surfactants, a preservative, a pH modifier and optionally a conditioner, with a viscosity adjusting system comprising glyceryl oleate and at least one additional viscosity adjusting agent.

In some embodiments, the personal care compositions of the present disclosure (i.e., Compositions 1, 1.1-1.20, 2, 2.1-2.19, 3 and 3.1-3.21) include a viscosity adjusting system comprising glyceryl oleate and at least one additional viscosity adjusting agent. In preferred embodiments, the personal care compositions are shampoos, shower gels, or face washes.

The personal care compositions of the present disclosure also include a surfactant system that is preferably comprised of an anionic surfactant and, for the shampoo compositions of the present disclosure (i.e., Compositions 1 or 1.1-1.20), an amphoteric surfactant. The surfactant systems of the shower gels (i.e., Compositions 2 or 2.1-1.19) and face washes (i.e., Compositions 3 or 3.1-1.21) of the present disclosure are preferably comprised of an anionic surfactant, a zwitterionic surfactant, and a nonionic surfactant.

In some embodiments of the shampoo, shower gel and face wash compositions of the disclosure, the surfactant system comprises about 5 wt % to about 15 wt %, about 7 wt % to about 13 wt %, about 8 wt % to about 12 wt %, about 9-11 wt %, or about 10-11 wt %, or about 10 wt % of the composition, or about 11 wt % of the composition.

Suitable anionic surfactants for both the personal care and shampoo compositions of the present disclosure include, but are not limited to, those surface-active or detergent compounds that contain an organic hydrophobic group containing generally 8 to 26 carbon atoms or generally 10 to 18 carbon atoms in their molecular structure and at least one water-solubilizing group selected from sulfonate, sulfate, and carboxylate so as to form a water-soluble detergent. Usually, the hydrophobic group will comprise a $C_8$-$C_{22}$ alkyl, or acyl group. Such surfactants are employed in the form of water-soluble salts and the salt-forming cation usually is selected from sodium, potassium, ammonium, magnesium and mono-, di- or tri-$C_2$-$C_3$ alkanolammonium, with the sodium, magnesium and ammonium cations again being the usual ones chosen.

Some examples of suitable anionic surfactants include, but are not limited to alkyl ether sulfates, for example linear $C_8$-$C_{18}$ alkyl ether sulfates, and salts thereof, preferably the sodium, potassium, ammonium, and ethanolammonium salts thereof.

Suitable anionic ether sulfates have the formula $R(OC_2H_4)_n$—$OSO_3M$ wherein n is 1 to 12, or 1 to 5, and R is an alkyl, alkylaryl, acyl, or alkenyl group having 8 to 18 carbon atoms, for example, an alkyl group of $C_{12}$-$C_{14}$ or $C_{12}$-$C_{16}$, and M is a solubilizing cation selected from sodium, potassium, ammonium, magnesium and mono-, di- and triethanol ammonium ions. Exemplary alkyl ether sulfates contain 12 to 15 carbon atoms in the alkyl groups thereof, e.g., sodium laureth (2 EO) sulfate. Some preferred exemplary anionic surfactants that may be used in the compositions of the present disclosure include sodium laurel ether sulfate (sodium laureth sulfate; SLES), sodium lauryl sulfate, and ammonium lauryl sulfate.

Preferably, the present personal care compositions comprise a single anionic surfactant. In some embodiments, the anionic surfactant is present in an amount of about 0.01 wt % to about 20 wt %, about 0.1 wt % to about 10 wt %, about 3 wt % to about 10 wt %, about 5 wt % to about 10 wt %, about 6 wt % to about 10 wt %, about 7 wt % to about 9 wt %, or about 7 wt %, about 8 wt %, or about 9 wt % of the composition.

In some embodiments, the personal care compositions of the present disclosure include a zwitterionic surfactant. Suitable zwitterionic surfactants include betaines and sultaines. In some embodiments, the zwitterionic surfactant comprises a betaine having a quaternary ammonium or phosphonium ion as the cationic group and a carboxylate group as the anionic group; for comprises a betaine having a quaternary ammonium ion as the cationic group and a carboxylate group as the anionic group (i.e., a quaternary ammonium carboxylate betaine). Typical alkyldimethyl betaines include, but are not limited to, decyl dimethyl betaine or 2-(N-decyl-N, N-dimethylammonia)acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include, but are not limited to, cocoamidoethylbetaine, cocoamidopropyl betaine and the like. In one embodiment, the betaine is coco ($C_8$-$C_{18}$) amidopropyl dimethyl betaine. Two examples of betaine surfactants that can be used are EMPIGEN™ BS/CA from Huntsman, and Tegobetaine F50 from BASF. One preferred zwitterionic surfactant is cocamidopropyl betaine. Other suitable zwitterionic surfactants include amine oxides.

In some embodiments, the shower gel and face wash compositions of the present disclosure preferably comprise a single zwitterionic surfactant. In some embodiments, the zwitterionic surfactant is present in an amount of about 0.01 wt % to about 10 wt %, about 0.5 wt % to about 5 wt %, about 1 wt % to about 3 wt %, about 1 wt % to about 2 wt %, or about 2 wt % to about 3 wt %, by weight of the composition.

In some embodiments, the shampoo compositions of the present disclosure include an amphoteric surfactant. As used herein, the term amphoteric surfactant is intended to mean a zwitterionic surfactant other than a quaternary ammonium surfactant. Suitable amphoteric surfactants include amine carboxylates, for example tertiary amine carboxylates, including N,N-disubstituted glycine derivatives, for example N-(2-aminoethyl)-N-(2-hydroxyethyl) glycine derivatives such as cocoamphoacetate salts, for example sodium cocoamphoacetate.

The shampoo compositions of the present disclosure preferably comprise a single amphoteric surfactant. In some embodiments, the amphoteric surfactant is present in an amount of about 0.5 wt % to about 5 wt %, about 1 wt % to about 4 wt %, about 2 wt % to about 3 wt %, or about 2.5 wt % to about 3 wt % of the composition.

In some embodiments of the shampoo compositions of the present disclosure, the surfactant system comprises an anionic surfactant and an amphoteric surfactant in a weight ratio of anionic surfactant to amphoteric surfactant of from about 1:1 to about 4:1, about 1.5:1 to about 3.5:1, about 2:1 to about 3:1, or about 2.5:1 by weight, based on the active weight of the surfactant.

The shampoo compositions of the present disclosure include a thickening system that includes glyceryl oleate. Glyceryl oleate (CAS Reg. No. 25496-72-4; glyceryl monooleate) is a known emollient and emulsifier. However, it has been discovered in accordance with the present disclosure that glyceryl oleate is also a viscosity adjusting (thickening) agent, and acts synergistically with other thickeners to afford viscosities that would otherwise not be possible. Thus, in some embodiments, the thickening system includes glyceryl oleate and an additional viscosity adjusting agent. The additional viscosity adjusting agent can be any viscosity adjusting or thickening agent known to be useful in shampoo formulations. Although these thickening agents can include inorganic salts such a sodium chloride, which are routinely used to enhance viscosities in personal care compositions, the use of such inorganic salts is disadvantageous in that the salt imparts corrosive properties to the formulation, making their contact with metals, such as metal springs, problematic. One benefit afforded by the use of glyceryl oleate in accordance with the present disclosure is that high viscosities are achieved using glyceryl oleate and either a viscosity adjusting agent that is not an inorganic salt, or, if an inorganic salt such as sodium chloride is used, significantly less salt is required to achieve high viscosities, resulting in less corrosive formulations. Accordingly, suitable viscosity adjusting (or thickening) agents for use in the thickening systems disclosed herein with glyceryl oleate include lipid thickeners such as cetyl alcohol, stearyl alcohol, carnauba wax, and stearic acid; natural thickeners such as hydroxyethylcellulose, guar gum, locust bean gum, xanthan gum, and gelatin; mineral thickeners such as silica, bentonite, and magnesium aluminum silicate; and synthetic thickeners such as carbomer thickeners. One preferred thickener system is glyceryl oleate and Glucamate™ LT, which is a mixture of PEG-120 methyl glucose trioleate, propylene glycol and water sold by Lubrizol Corp., Wickliffe, Ohio. In some preferred embodiments of the shampoo compositions of the present disclosure, the glyceryl oleate is present in an amount of from 0.1-1% by weight of the composition, for example from 0.2-0.8% by weight of the composition, for example from 0.3-0.7% by weight of the composition, for example about 0.5% by weight of the composition; and the Glucamate™ LT is present in an amount of from 0.1-2.5% by weight of the composition; for example 0.5-2% by weight of the composition, for example 0.75-1.5% by weight of the composition, for example 0.8-1.2% by weight of the composition, for example about 1% by weight of the composition.

In some embodiments, preservatives are included in the present personal care and shampoo compositions, preferably at a concentration of about 0.01 wt % to about 10 wt %, about 0.01 wt % to 3 wt %, or 0.01 wt % to 2.5 wt %. Examples of preservatives include, but are not limited to, benzalkonium chloride; sodium benzoate, sodium salicylate; benzethonium chloride, 5-bromo-5-nitro-1,3dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl) urea; 1-3-dimethyol-5,5-dimethyl hydantoin; formaldehyde; iodopropynyl butyl carbamate, butyl paraben; ethyl paraben; methyl paraben; propyl paraben, mixture of methyl isothiazolinone/methyl-chloroisothiazoline in a 1:3 wt. ratio; mixture of phenoxyethanol/butyl paraben/methyl paraben/propylparaben; 2-phenoxyethanol; tris-hydroxyethylhexahydrotriazine; methylisothiazolinone; 5-chloro-2-methyl-4-isothiazolin-3-one; 1,2-dibromo-2,4-dicyanobutane; 1-(3-chloroalkyl)-3,5,7-triazaazoniaadamantane chloride; organic acids, lactic acid, or citric acid and combinations thereof.

In some preferred embodiments of the shampoo compositions of the present disclosure, the compositions contain a preservative system that includes at least two preservatives, for example phenoxyethanol and sodium benzoate in a weight ratio of from 0.8:1 to 1.2:1, for example about 1:1, and preferably a combined amount of the preservatives of from about 0.1 to about 1.5%, for example from about 0.4-1.2%, for example from about 0.6-1%, for example about 0.8% by weight of the composition.

In some preferred embodiments of the shower gel and face wash compositions of the present disclosure, the compositions contain a preservative system that includes at least two preservatives, for example sodium benzoate and sodium salicylate in a weight ratio of from 1:1 to 2:1, for example from 1:1 to 1.5:1; for example from 1.3:1 to 1.4:1 by weight of the composition. In some embodiments, the at least two preservatives are present in a combined amount of from about 0.1 to about 1.5%, for example from about 0.4-1.2%, for example from about 0.5-1%, for example about 0.7% by weight of the composition.

pH modifying agents include acidifying agents to lower pH, basifying agents to raise pH and buffering agents to control pH within a desired range. For example, one or more compounds selected from acidifying, basifying and buffering agents can be included to provide a pH of 2 to 10, or in various illustrative embodiments 2 to 8, 3 to 9, 4 to 8, 5 to 7, 6 to 10, 7 to 9, etc. In preferred embodiments, the pH is between about 1 to 5, about 2 to 5, about 4 to 5, or about 4.2-4.8. Examples of pH modifying agent include HCl, phosphoric and sulfonic acids and carboxylic acids such as lactic acid and citric acid, acid salts (e.g., monosodium citrate, disodium citrate, sodium lactate, monosodium malate, etc.), alkali metal hydroxides such as sodium hydroxide and potassium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an acceptable pH range. Preferably, only one or two pH modifying agents are employed. In some preferred embodiments of the shampoo, shower gel and face wash compositions of the present disclosure, the pH modifier is lactic acid, sodium lactate, or a combination of both lactic acid and sodium lactate.

In certain embodiments, the personal care composition is in the form of a cleansing liquid.

In some embodiments, shampoo, shower gel and face wash compositions of the present disclosure can optionally include an emollient or moisturizer component. Illustrative examples of such emollient components include glycerine, glyceryl oleate, caprylyl glycol, triglycerides (e.g., caprylic/capric triglyceride), silicone oils (e.g., cyclomethicone), ester oils (e.g., butyl myristate, isopropyl myristate, cetyl myristate, isopropyl palmitate, isopropyl stearate, octyl stearate, isocearyl stearate), organic fatty alcohols (e.g., oleic alcohol, linolenic alcohol, linoleic alcohol, isostearyl alcohol, octyl dodecanol), long chain fatty acids, liquid water-soluble polyols, propylene glycol, sorbitol, polyethylene glycol, ethoxylated/propoxylated ethers of methyl glucose (eg., methyl gluceth-20) and ethoxylated/-propoxylated ethers of lanolin alcohol (e.g., Solulan-75), coco and tallow fatty acids, nonoclusive liquid water soluble polyols, essential amino acids, and sodium pyrrolidone carboxylic acid (or sodium dl-pyrrolidone carboxylate), urea, L-proline, guanidine and pyrrolidone; hexadecyl, myristyl, isodecyl or isopropyl esters of adipic, lactic, oleic, stearic, isostearic, myristic or linoleic acids and corresponding alcohol esters such as sodium isostearoyl-2 lactylate, sodium capryl lactylate, aloe vera gel and acetamide MEA. The shampoo compositions of the present disclosure can also include an emollient or moisturizer component in addition to the glyceryl oleate, which can be any of the foregoing emollients or moisturizers.

In some embodiments, the shampoo compositions of the present disclosure further include an anti-dandruff active. Suitable non-limiting examples of anti-dandruff actives include active substances such as piroctone olamine, zinc omadine, and climbazole, pyridinethione salts, azoles, selenium sulfide, particulate sulfur, keratolytic agents, and mixtures thereof. Such anti-dandruff actives should be physically and chemically compatible with the essential components of the composition, and should not otherwise unduly impair product stability, aesthetics or performance. When present in the composition, the anti-dandruff active is included in an amount from about 0.01% to about 3%, preferably from about 0.1% to about 2%, and more preferably from about 0.3% to about 0.8%, or about 0.5% by weight of the composition.

In some embodiments, the shampoo compositions of the present disclosure further include a film forming and/or conditioner polymer. Suitable polymers include polyquaternium polymers, for example polyquaternium 10, for example in an amount of from about 0.1-0.8%, or from about 0.2%-0.6%, or about 0.4% by weight of the composition.

In some embodiments, the shower gel, face wash and shampoo compositions of the present disclosure further include one or more optional ingredients selected from coloring agents, fragrances, moisturizing agents, and amino acids, vitamins, extracts, proteins, antioxidants, pearlizers, opacifiers, and a combination of two or more thereof.

Further optional ingredients can also be present in the personal care compositions described herein. Non-limiting examples of further optional ingredients include skin conditioning agents, moisturizing agents, fragrance, dyes and pigments, titanium dioxide, chelating agents such as EDTA, sunscreen active ingredients such as butyl methoxy benzoylmethane; antiaging compounds such as alpha hydroxy acids, beta hydroxy acids; antioxidants such as butylated hydroxytoluene (BHT); vitamins such as A, E, K and C; essential oils and extracts thereof such as rosewood and jojoba, free fatty acids to provide enhanced skin feel benefits such as softer or smoother feeling skin, for example free fatty acids include those derived from tallow, coconut oil, palm oil and palm kernel oil, and mixtures of any of the foregoing components.

In some embodiments, the personal care compositions optionally include fragrance in an amount of about 0.01 wt % to about 4 wt % by weight of the composition, preferably about 0.1 wt % to about 2 wt %, more preferably about 0.2 wt % to about 1.5 wt %.

In some embodiments, the shampoo or personal care compositions optionally include pearlizers, such as Styrene/Acrylates Copolymer or glycol distearate, in an amount of about 0.01 wt % to 3 wt % by weight.

The shampoo or personal care compositions of the present disclosure preferably include water as a carrier; i.e., added water (i.e., water separately added, not including water added consequent to addition of a solution of another component), e.g., in an amount of from 5-95%, 50%-95%, 60%-80%, 60%-85%, 65%-75%, 68%-72%, or about 70% by weight of the composition.

The personal care compositions of the present disclosure may be prepared by any ordinary methods known in the art. For example, the composition may be prepared by mixing the anionic surfactant into a suitable aqueous carrier. The components are mixed for a period of time sufficient for complete incorporation. Once mixture is complete, the zwitterionic surfactant is added to the mixture, and the components are again mixed for a suitable period of time. Following addition of the surfactants, a preservative is added with an accompanying appropriate mixing process. A pH modifier is added to the mixture until desired pH level is achieved. A rheology modifier is added to achieve a desired viscosity, and the final mixture is mixed for an appropriate amount of time until the ingredients are homogenously dispersed.

Exemplary embodiments of the present disclosure will be illustrated by reference to the following examples, which are included to exemplify, but not to limit the scope of the present invention.

EXAMPLES

Example 1

Tables 1 and 2 describes generic and specific formulas of exemplary shampoo compositions according to the present disclosure containing the present glyceryl oleate viscosity adjusting system.

TABLE 1

| Function | Ingredient | Composition A (wt %) |
|---|---|---|
| N/A | Water | 65-75 |
| Surfactant | Sodium Laureth Sulfate (70%) | 5-10 |
| Surfactant | Sodium Cocoamphoacetate (32%) | 1-4 |
| Pearlizer/Opacifier | Pearlizer/Opacifier | 2-6 |
| pH modifier | Lactic Acid (50%) | 0.1-2 |
| Moisturizer | Sodium dl-Pyrrolidone Carboxylate (50%) | 0.01-0.8 |
| Preservative | Sodium Benzoate | 0.1-0.8 |
| Viscosity adjuster/ emollient | Glyceryl Oleate | 0.1-1 |
|  | Vitamins/Extracts/Protein/ Fragrance | 0.5-1.5 |
| Anti-oxidant | Tocopheryl Acetate | 0.01-2.5 |
| Thickener/Viscosity Adjusting Agent | Glucamate LT | 0.1-2.5 |
| Active (anti-dandruff) | Piroctone Olamine (Octopirox) | 0.2-1 |
| Preservative | Phenoxy Ethanol | 0.1-1 |
| Film Former/ Conditioner | Polymer JR 400 (Polyquaternium 10) | 0.1-1 |

TABLE 2

| Function | Ingredient | Composition B (wt % active) |
|---|---|---|
| N/A | Water | 69.7 |
| Surfactant | Sodium Laureth Sulfate (70%) | 7.14 |
| Surfactant | Sodium Cocoamphoacetate (32%) | 2.88 |
| Pearlizer/Opacifier | Pearlizer/Opacifier | 4 |
| pH modifier | Lactic Acid (50%) | 1.11 |
| Moisturizer | Sodium dl-Pyrrolidone Carboxylate (50%) | 0.25 |
| Preservative | Sodium Benzoate | 0.4 |
| Viscosity adjuster/ emollient | Glyceryl Oleate | 0.5 |
|  | Vitamins/Extracts/Protein/ Fragrance | 1.067 |
| Anti-oxidant | Tocopheryl Acetate | 0.1 |
| Thickener/Viscosity Adjusting Agent | Glucamate LT | 1.0 |
| Active (anti-dandruff) | Piroctone Olamine (Octopirox) | 0.5 |
| Preservative | Phenoxy Ethanol | 0.4 |
| Film Former/ Conditioner | Polymer JR 400 (Polyquaternium 10) | 0.4 |

The exemplary compositions described in Tables 1 and 2 above may be prepared according to conventional methods known to those skilled in the art. In particular, the exemplary composition of the present invention is prepared to ensure that the surfactant system provides the anionic and amphoteric surfactants at certain weight ratios. The sodium laureth sulfate is provided in the form of a diluted solution containing 70% by weight of sodium laureth sulfate; and the sodium cocoamphoacetate is provided in the form of a diluted solution containing 32% by weight of sodium cocoamphoacetate; and the lactic acid is provided in the form of a diluted solution containing 50% by weight of lactic acid.

The formulation of Table 1 has a white, pearlized appearance, a pH of from 4.4-4.9, and a viscosity (Brookfield DV-II+ Viscometer, 24 hours, Sp #4, 20 RPM, 25° C.) of 3,000-6,000 cp.

The surfactant system includes sodium laureth sulfate as the anionic surfactant and sodium cocoamphoacetate as the zwitterionic surfactant, and the thickening system includes glyceryl oleate and Glucamate™ LT thickener, which is a mixture of PEG-120 methyl glucose trioleate; propylene glycol and water sold by Lubrizol.

Example 2

Viscosities were determined for a commercial antidandruff shampoo alone; the same shampoo with 1% Glucamate™ LT; the same shampoo with 0.5% glyceryl oleate; and the same shampoo with both 1% Glucamate™ LT and 0.5% glyceryl oleate. The results are shown below in Table 3:

TABLE 3

| Shampoo | Viscosity (cp) |
|---|---|
| Commercial antidandruff shampoo alone | 1780 |
| Commercial antidandruff shampoo with 1% Glucamate ™ LT | 2740 |
| Commercial antidandruff shampoo with 0.5% glyceryl oleate | 2780 |
| Commercial antidandruff shampoo with 1% Glucamate ™ LT and 0.5% glyceryl oleate | 4880 |

It can be seen that the combination of 1% Glucamate™ LT and 0.5% glyceryl oleate (increase of 3100 cp) provides an increase in viscosity that is greater than the sum of the increases in viscosity caused by both individually (increase of 960 cp and 1000 cp for 1% Glucamate™ LT and 0.5% glyceryl oleate, respectively).

Further studies were undertaken wherein the effect of increasing weight percent of Glucamate™ LT was determined on the viscosities of the same commercial antidandruff shampoo alone and with 0.5% glyceryl oleate. The viscosities were determined on a Brookfield DV-II+ Viscometer, at 24 hours, Sp #4, 20 RPM, 25° C. The results are shown below in Table 4:

TABLE 4

| Weight % Glucamate ™ LT | Commercial antidandruff shampoo alone | Commercial antidandruff shampoo with 0.5% glyceryl oleate |
|---|---|---|
| 0 | 1780 | 2780 |
| 0.2 | 2100 | 3450 |
| 0.4 | 2310 | 3840 |
| 0.5 | 2440 | 4080 |
| 0.8 | 2590 | 4380 |
| 1 | 2740 | 4880 |
| 1.2 | 3050 | 5460 |

It can be seen that over the range of 0%-1.2% Glucamate™ LT, the viscosity of the commercial antidandruff shampoo alone increased by 1270 cp, whereas the viscosity of the commercial antidandruff shampoo containing 0.5% glyceryl oleate increased by 2680 cp. The addition of the glyceryl oleate allowed to reach viscosity levels that was not possible with Glucamate LT, a known thickener, alone.

Example 3

Tables 5 and 6 describes generic and specific formulas of exemplary shower gel and face wash compositions according to the present disclosure containing the present glyceryl oleate viscosity adjusting system.

TABLE 5

Exemplary Shower Gel and Face Wash Compositions

| Function | Ingredient | Comp. C (Dermo Comfort Dry Shower Gel) (wt %) | Comp. D (Dermo Protect Normal Face Wash) (wt %) | Comp. E (Dermo Sensitive (Sensitive) Face Wash) (wt %) | Comp. F (Zero % Face Wash) (wt %) |
|---|---|---|---|---|---|
| N/A | Water | 60-80 | 60-80 | 60-80 | 60-80 |
| Surfactant | Sodium Laureth Sulfate (70%) | 7-9 | 6.5-8.5 | 6.5-8.5 | 6.5-9 |
| Surfactant | Cocamidopropyl Betaine (30%) | 0.5-2.5 | 1-4 | 1-4 | 0.5-2.5 |
| Surfactant | Coco-Glucoside | 0.5-3 | 0.5-3 | 0.5-3 | 0.5-3 |
| Humectant | Glycerin | 5-9 | 0.5-4 | 5-9 | 5-9 |
| Skin Conditioner | Polyquaternium 7 | 0 | 0.001-3 | 0 | 0 |
|  | Opacifier/Fragrance | 0.1-3 | 0 | 0 | 0 |
| Emollient | Caprylyl glycol | 0.01-0.3 | 0 | 0.01-0.3 | 0 |
| Viscosity adjuster/ emollient | Glyceryl Oleate | 0.1-1 | 0.01-0.5 | 0.01-0.5 | 0.01-0.5 |
| Skin flora regulator | Zinc sulfate (50%) | 0.01-0.3 | 0 | 0.01-0.3 | 0 |
| Viscosity adjuster | Sodium Chloride (Q.S.) | 0.1-1 | 0.1-1 | 0.1-1 | 0.1-1 |
| Thickener/ Viscosity Adjusting Agent | Glucamate LT | 0 | 0 | 0.1-1 | 0.1-1 |
| Preservative | Sodium Benzoate powder 100% | 0.1-1 | 0.1-1 | 0.1-1 | 0.1-1 |
| Preservative | Sodium salicylate powder 100% | 0.1-1 | 0.1-1 | 0.1-1 | 0.1-1 |
| pH modifier | Lactic Acid (50%) | 0.5-3 | 0.5-3 | 0.5-3 | 0.5-2 |
| pH modifier | Sodium lactate | 0.5-3 | 0.5-3 | 0.5-3 | 0.5-3 |

TABLE 6

Exemplary Shower Gel and Face Wash Compositions

| Function | Ingredient | Comp. G (Dermo Comfort Dry Shower Gel) (wt %) | Comp. H (Dermo Protect Normal Face Wash) (wt %) | Comp. I (Dermo Sensitive (Sensitive) Face Wash) (wt %) | Comp. J (Zero % Face Wash) (wt %) |
|---|---|---|---|---|---|
| N/A | Water | 68.06 | 71.8 | 67.575 | 70.15 |
| Surfactant | Sodium Laureth Sulfate (70%) | 8.19 | 7.35 | 7.35 | 7.00 |
| Surfactant | Cocamidopropyl Betaine (30%) | 1.38 | 2.31 | 2.31 | 1.74 |

TABLE 6-continued

Exemplary Shower Gel and Face Wash Compositions

| Function | Ingredient | Comp. G (Dermo Comfort Dry Shower Gel) (wt %) | Comp. H (Dermo Protect Normal Face Wash) (wt %) | Comp. I (Dermo Sensitive (Sensitive) Face Wash) (wt %) | Comp. J (Zero % Face Wash) (wt %) |
|---|---|---|---|---|---|
| Surfactant | Coco-Glucoside (50%) | 1.25 | 1.25 | 1.25 | 1.25 |
| Humectant | Glycerin | 7.25 | 2.00 | 7.00 | 7.00 |
| Skin Conditioner | Polyquaternium 7 | 0 | 0.0089 | 0 | 0 |
| Opacifier | Opacifier | 1.20 | 0 | 0 | 0 |
|  | Fragrance | 0.5 | 0.450 | 0.450 | 0.350 |
| Emollient | Caprylyl glycol | 0.10 | 0 | 0.10 | 0 |
| Viscosity adjuster/emollient | Glyceryl Oleate | 0.50 | 0.25 | 0.25 | 0.25 |
| Skin flora regulator | Zinc sulfate (50%) | 0.05 | 0 | 0.05 | 0 |
| Viscosity adjuster | Sodium Chloride (Q.S.) | 0.440 | 0.750 | 0.375 | 0.750 |
| Thickener/Viscosity Adjusting Agent | Glucamate LT | 0 | 0 | 0.400 | 0.400 |
| Preservative | Sodium Benzoate powder 100% | 0.4 | 0.4 | 0.4 | 0.4 |
| Preservative | Sodium salicylate powder 100% | 0.3 | 0.3 | 0.3 | 0.3 |
| pH modifier | Lactic Acid (50%) | 0.575 | 0.575 | 0.575 | 0.45 |
| pH modifier | Sodium lactate | 0.72 | 0.72 | 0.72 | 0.72 |
| pH |  |  | 4.2-4.6 | 4.2-4.6 | 4.2-4.8 |
| CP Viscosity (25° C., SP #4, 20 RPM) |  | 4000-7000 | 15,000-25,000 | 15,000-25,000 | 15,000-25,000 |

The exemplary compositions described in Tables 5 and 6 above may be prepared according to conventional methods known to those skilled in the art. In particular, the exemplary composition of the present invention is prepared to ensure that the surfactant system provides the anionic and zwitterionic surfactants at certain weight ratios. The sodium laureth sulfate is provided in the form of a diluted solution containing 70% by weight of sodium laureth sulfate; the cocamidopropyl betaine is provided in the form of a diluted solution containing 30% by weight of cocamidopropyl betaine; the coco-glucoside is provided in the form of a diluted solution containing 50% by weight of coco-glucoside; and the lactic acid is provided in the form of a diluted solution containing 50% by weight of lactic acid.

The surfactant system includes sodium laureth sulfate as the anionic surfactant, cocamidopropyl betaine as the zwitterionic surfactant, and coco-glucoside as the nonionic surfactant. The viscosity adjusting (thickening) system includes glyceryl oleate and sodium chloride, and in two face wash formulations (Compositions I and J) Glucamate™ LT thickener.

The compositions have high viscosities and excellent rheological properties.

Example 4

Viscosities were determined for the shower gel of Composition G above with and without 0.5% glyceryl oleate at various Table Salt concentrations. The results are shown below in Table 7:

TABLE 7

| % Table Salt Solution | Composition G Shower Gel without Glyceryl Oleate | Composition G Shower Gel with 0.5% Glyceryl Oleate |
|---|---|---|
| 0.00 | 2030 | 18020 |
| 0.50 | 3080 | 26080 |
| 0.75 | 3810 | 28600 |
| 1.00 | 4570 | 29600 |
| 1.25 | 5060 | 29600 |
| 1.50 | 6020 | 26280 |
| 1.75 | 6760 | 25480 |
| 2.00 | 7800 | 17500 |
| 2.25 | 8910 | 15340 |
| 2.50 | 8340 | 13560 |
| 2.75 | 9240 | 8760 |
| 3.00 | 9780 | 8760 |
| 3.50 | 12760 | 4840 |
| 4.00 | 12720 | 2550 |
| 4.50 | 12920 | 1640 |
| 5.00 | 11600 | 2160 |
| 5.50 | 10020 | 950 |

The viscosities were determined as described above (Brookfield DV-II+ Viscometer, 24 hours, Sp #4, 20 RPM, 25° C.). It can be seen that the presence of 0.5% glyceryl oleate provides a significant increase in viscosity at relatively low salt concentrations.

Example 5

Viscosities were determined for the Face Wash of Composition I above with and without 0.5% glyceryl oleate at various Table Salt concentrations. The results are shown below in Table 8A:

TABLE 8A

| % Table Salt Solution | Composition I Face Wash without Glyceryl Oleate | Composition G Face Wash with 0.5% Glyceryl Oleate |
| --- | --- | --- |
| 0.00 | 2930 | 11820 |
| 0.50 | 4000 | 11940 |
| 0.75 | 4650 | 11640 |
| 1.00 | 5300 | 10840 |
| 1.25 | 5450 | 9980 |
| 1.50 | 5940 | 8900 |
| 1.75 | 6780 | 8220 |
| 2.00 | 6870 | 7220 |
| 2.25 | 6870 | 6660 |
| 2.50 | 7870 | 5480 |
| 2.75 | 7600 | 4540 |
| 3.00 | 8040 | 4060 |
| 3.50 | 8060 | 3520 |
| 4.00 | 7810 | 3560 |
| 4.50 | 7300 | 2580 |
| 5.00 | 6280 | — |
| 5.50 | 5660 | — |

The viscosities were determined as described above (Brookfield DV-II+ Viscometer, 24 hours, Sp #4, 20 RPM, 25° C.). It can be seen that the presence of 0.5% glyceryl oleate provides a significant increase in viscosity at relatively low salt concentrations.

Example 6

Viscosities were determined for the Face Wash of Composition I above at various brine concentrations with 0%, 0.25%, 0.4% and 0.5% glyceryl oleate (Table 7), and with 0% glyceryl oleate/0% Glucamate; 0% glyceryl oleate/0.25% Glucamate; and 0.25% glyceryl oleate/0.25% Glucamate (Table 8B). The viscosities were determined under the same conditions as described above.

TABLE 8B

Composition I Men's Face Wash—Glyceryl Oleate and Brine

| wt % Brine (25% sol) | Men's FW 0% Glyceryl Oleate | Men's FW 0.25% Glyceryl Oleate | Men's FW 0.4% Glyceryl Oleate | Men's FW 0.5% Glyceryl Oleate |
| --- | --- | --- | --- | --- |
| 0 | 3070 | 3078 | 4510 | 9110 |
| 1 | 5330 | 5360 | 7810 | 9040 |
| 2 | 7860 | 7860 | 11440 | 3230 |
| 3 | | 9590 | 12560 | 1870 |
| 4 | | 11040 | 10720 | |
| 5 | | 10080 | 7840 | |
| 6 | | 7940 | 4360 | |

It can be seen in Table 8B that the increase presence of glyceryl oleate provides a significant increase in viscosity at relatively low salt concentrations and that by increasing the level of glyceryl oleate one is able to decrease the level of sodium chloride required to thicken.

TABLE 8C

Composition I Men's Face Wash—Glyceryl Oleate and Glucamate

| wt % Brine (25% sol) | Men's FW 0% Glyceryl Oleate/0% Glucamate | Men's FW 0% Glyceryl Oleate/0.25% Glucamate | Men's FW 0.25% Glyceryl Oleate/0.25% Glucamate |
| --- | --- | --- | --- |
| 0 | 3070 | 9320 | 13180 |
| 1 | 5330 | 11800 | 15200 |
| 2 | 7860 | 13300 | 16460 |
| 3 | | 12340 | 14160 |
| 4 | | 16880 | 11680 |

It can be seen in Table 8C that the increase presence of glyceryl oleate provides a significant increase in viscosity of Glucamate LT alone.

Example 7

Viscosities were determined for the Face Wash of Composition H above at various brine concentrations with 0% and 0.25% glyceryl oleate. The results are shown in Table 9 below. The viscosities were determined under the same conditions as described above.

TABLE 9

Composition H Face Wash—Glyceryl Oleate and Brine

| wt % Brine (25% sol) | Men's FW 0% Glyceryl Oleate | Men's FW 0.25% Glyceryl Oleate |
| --- | --- | --- |
| 0 | | 3120 |
| 1 | | 6340 |
| 2 | | 9120 |
| 3 | 7120 | 14780 |
| 4 | 8940 | 17680 |
| 5 | 11600 | 18000 |
| 6 | 13640 | 19040 |

It can be seen in Table 9 that the increase presence of glyceryl oleate provides a significant increase in viscosity at relatively lower salt concentrations and allows one to achieve higher viscosities that are not possible without glyceryl oleate.

Example 8

Viscosities were determined for the Face Wash of Composition J above at various brine concentrations with 0%, 0.25% and 0.5% glyceryl oleate. The results are shown in Table 10 below. The viscosities were determined under the same conditions as described above.

TABLE 10

Composition J Face Wash—Glyceryl Oleate and Brine

| wt % Brine (25% sol) | Men's FW 0% Glyceryl Oleate | Men's FW 0.25% Glyceryl Oleate | Men's FW 0.5% Glyceryl Oleate |
| --- | --- | --- | --- |
| 0 | 550 | 550 | 4170 |
| 2 | | 2432 | 9700 |
| 4 | 3560 | 5050 | 13900 |
| 6 | 5250 | 7700 | 7180 |

It can be seen in Table 10 that the increase presence of glyceryl oleate provides a significant increase in viscosity at relatively low salt concentrations and that by increasing the level of glyceryl oleate one is able to decrease the level of sodium chloride required to thicken.

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

What is claimed is:

1. A personal care composition comprising:
   a surfactant system consisting essentially of:
      an anionic surfactant;
      a zwitterionic or amphoteric surfactant; and optionally a non-ionic surfactant;
   a preservative system;
   a pH modifier;
   optionally a moisturizer or a skin conditioner or both a moisturizer and a skin conditioner; and
   a viscosity adjusting system,
   wherein the viscosity adjusting system comprises glyceryl oleate and at least one additional viscosity adjusting agent selected from a mixture of PEG-120 methyl glucose trioleate and propylene glycol, and
   wherein the ingredients are homogenously dispersed.

2. The personal care composition of claim 1, wherein the viscosity adjusting system further comprises an additional viscosity adjusting agent selected from natural thickeners; mineral thickeners; synthetic thickeners; and inorganic salts.

3. The personal care composition of claim 1, wherein the viscosity adjusting system consists essentially of glyceryl oleate and a mixture, wherein said mixture is a mixture of PEG-120 methyl glucose trioleate, propylene glycol and water.

4. The personal care composition of claim 3, wherein the glyceryl oleate is present in an amount of from 0.2-0.8% by weight of the composition; and the mixture is present in an amount of from 0.1-2.5% by weight of the composition.

5. The personal care composition of claim 2, wherein the surfactant system consists essentially of an anionic surfactant and an amphoteric surfactant, and is free of other surfactants; and wherein the weight ratio of anionic surfactant to amphoteric surfactant is from about 1:1 to about 4:1, based on the active weight of the surfactant.

6. The personal care composition of claim 5, wherein:
   the anionic surfactant is an alkyl ether sulfate; and
   the amphoteric surfactant is a N,N-disubstituted glycine derivative; and
   wherein the surfactant system comprises about 5 to about 15% by weight of the personal care composition.

7. The personal care composition of claim 1, wherein the pH modifier is selected from lactic acid, sodium lactate, citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, and a combination of two or more thereof.

8. The personal care composition of claim 1, wherein the preservative system comprises one or more preservatives selected from sodium benzoate, sodium salicylate, benzalkonium chloride, benzethonium chloride, 5-bromo-5-nitro-1,3-dioxane, 2-bromo-2-nitropropane-1,3-diol, alkyl trimethyl ammonium bromide, N-(hydroxymethyl)-N-(1,3-dihydroxy methyl-2, 5-dioxo-4-imidaxolidinyl-N-(hydroxy methyl)urea, 1-3-dimethyol-5,5-dimethyl hydantoin, iodopropynyl butyl carbamate, butyl paraben, ethyl paraben, methyl paraben, propyl paraben, methyl isothiazolinone, methyl-chloroisothiazoline, phenoxyethanol, tris-hydroxy-ethyl-hexahydrotriazine, methylisothiazolinone, 5-chloro-2-methyl-4-isothiazolin-3-one, 1,2-dibromo-2,4-dicyanobutane, 1-(3-chloroalkyl)-3,5,7-triaza-azoniaadamantane chloride, organic acids, or combinations thereof.

9. The personal care composition of claim 1, wherein the preservative system comprises at least two preservatives.

10. The personal care composition of claim 1, comprising a moisturizer and a conditioner.

11. The personal care composition of claim 3, wherein the personal care composition is a shampoo composition and further comprises an anti-dandruff active; and also further comprises one or more optional ingredients selected from fragrances, vitamins, extracts, proteins, antioxidants, pearlizers, opacifiers and a combination of two or more thereof.

12. The shampoo composition of claim 11, comprising added water in an amount of from 65% to 75% by weight of the composition.

13. A method of cleansing hair comprising applying to the hair a composition according to claim 1.

14. A personal care composition comprising:
   a surfactant system consisting essentially of:
      an anionic surfactant;
      a zwitterionic surfactant; and
      a non-ionic surfactant;
   a preservative system;
   a pH modifier;
   optionally a moisturizer or a skin conditioner or both a moisturizer and a skin conditioner; and
   a viscosity adjusting system,
   wherein the weight ratio of anionic surfactant to zwitterionic surfactant to non-ionic surfactant is about (5.5-7.5):(0.5-1.5):(0.8-1.2) by weight, based on the active weight of the surfactant,
   wherein the viscosity adjusting system consists essentially of glyceryl oleate, a mixture of PEG-120 methyl glucose trioleate and propylene glycol, and an inorganic salt; wherein the glyceryl oleate is present in an amount of from 0.1-1% by weight of the composition; and the inorganic salt is present in an amount of from 0.1-1.5% by weight of the composition, and
   wherein the ingredients are homogenously dispersed.

15. The personal care composition of claim 14, wherein the inorganic salt is sodium chloride, wherein the glyceryl oleate is present in an amount of from about 0.3-0.7% by weight of the composition, and wherein the sodium chloride is present in an amount of 0.3-0.8% by weight of the composition.

16. The personal care composition of claim 14, wherein the weight ratio of anionic surfactant to zwitterionic surfactant to non-ionic surfactant is (6-7):(1-1.3):(0.9-1.1) by weight, based on the active weight of the surfactant.

17. The personal care composition of claim 15, wherein:
   the anionic surfactant is an alkyl ether sulfate;
   the zwitterionic surfactant is a quaternary ammonium carboxylate betaine;
   the non-ionic surfactant is selected from ethoxylated aliphatic alcohols, alkyl glucosides, polyoxyethylene surfactants, carboxylic esters, polyethylene glycol esters, anhydrosorbitol ester and it's ethoxylated derivatives, glycol esters of fatty acids, carboxylic amides, monoalkanolamine condensates and polyoxyethylene fatty acid amides; and
   the surfactant system comprises about 5 to about 15%, about 7 to about 13%, about 8 to about 12%, about 9-11%, or about 10-11%, or about 10%, or about 11%, by weight of the personal care composition.

18. The personal care composition of claim 14, wherein the pH modifier is selected from lactic acid, sodium lactate, citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, and a combination of two or more thereof.

19. The personal care composition of claim 14, wherein the preservative system comprises one or more preservatives selected from sodium benzoate, sodium salicylate, benzalkonium chloride, benzethonium chloride, 5-bromo-5-nitro-1,3-dioxane, 2-bromo-2-nitropropane-1,3-diol, alkyl trimethyl ammonium bromide, N-(hydroxymethyl)-N-(1,3-dihydroxy methyl-2,5-dioxo-4-imidaxolidinyl-N-(hydroxy methyl)urea, 1-3-dimethyol-5,5-dimethyl hydantoin, iodopropynyl butyl carbamate, butyl paraben, ethyl paraben, methyl paraben, propyl paraben, methyl isothiazolinone, methyl-chloroisothiazoline, phenoxyethanol, tris-hydroxy-ethyl-hexahydrotriazine, methylisothiazolinone, 5-chloro-2-methyl-4-isothiazolin-3-one, 1,2-dibromo-2,4-dicyanobutane, 1-(3-chloroalkyl)-3,5,7-triaza-azoniaadamantane chloride, organic acids, or combinations thereof.

20. The personal care composition of claim 14, wherein the preservative system comprises at least two preservatives.

21. The personal care composition of claim 14, wherein the personal care composition is a shower gel composition.

22. The shower gel composition of claim 21, further comprising a zinc salt skin flora regulator active; and
further comprising caprylyl glycol active; and
optionally further comprising a humectant selected from glycerin, lactic acid, propylene glycol, sodium PCA, sorbitol, and mixtures thereof; and
optionally further comprising one or more optional ingredients selected from fragrances, vitamins, extracts, proteins, antioxidants, pearlizers, opacifiers and a combination of two or more thereof.

23. A personal care composition comprising:
a surfactant system consisting essentially of:
   an anionic surfactant;
   a zwitterionic or amphoteric surfactant; and optionally
   a non-ionic surfactant;
a preservative system;
a pH modifier;
optionally a moisturizer or a skin conditioner or both a moisturizer and a skin conditioner; and
a viscosity adjusting system,
wherein the viscosity adjusting system consists essentially of glyceryl oleate, sodium chloride and a mixture of PEG-120 methyl glucose trioleate, propylene glycol and water; wherein:
the glyceryl oleate is present in an amount of from 0.1-0.8% by weight of the composition;
the sodium chloride is present in an amount of from 0.1-1.25% by weight of the composition; and
the mixture is optionally present in an amount of about 0.1-0.8% by weight of the composition, and
wherein the ingredients are homogenously dispersed.

24. The personal care composition of claim 23, wherein:
the glyceryl oleate is present in an amount of from 0.2-0.3% by weight of the composition;
the sodium chloride is present in an amount of from about 0.7-0.8% by weight of the composition, or from about 0.3-0.45% by weight of the composition; and
the mixture is optionally present in an amount of from about 0.1-0.8% by weight of the composition.

25. The personal care composition of claim 23, wherein the surfactant system consists essentially of an anionic surfactant, a zwitterionic surfactant, and a nonionic surfactant; wherein:
the weight ratio of anionic surfactant to zwitterionic surfactant to non-ionic surfactant is from about (4.5-7):(1-3):(0.8-1.2), based on the active weight of the surfactant;
the anionic surfactant is an alkyl ether sulfate;
the zwitterionic surfactant is a quaternary ammonium carboxylate betaine; and
the non-ionic surfactant is selected from ethoxylated aliphatic alcohols, alkyl glucosides, polyoxyethylene surfactants, carboxylic esters, polyethylene glycol esters, anhydrosorbitol ester and it's ethoxylated derivatives, glycol esters of fatty acids, carboxylic amides, monoalkanolamine condensates and polyoxyethylene fatty acid amides; and
wherein the surfactant system comprises about 5 wt % to about 15 wt %, about 7 wt % to about 13 wt %, about 8 wt % to about 12 wt %, about 9-11 wt %, or about 10-11 wt %, or about 10 wt % of the composition, or about 11 wt % of the composition.

26. The personal care composition of claim 23, wherein:
the pH modifier is selected from lactic acid, sodium lactate, citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, and a combination of two or more thereof; and
the preservative system comprises at least two preservatives selected from sodium benzoate, sodium salicylate, benzalkonium chloride, benzethonium chloride, 5-bromo-5-nitro-1,3-dioxane, 2-bromo-2-nitropropane-1,3-diol, alkyl trimethyl ammonium bromide, N-(hydroxymethyl)-N-(1,3-dihydroxy methyl-2, 5-dioxo-4-imidaxolidinyl-N-(hydroxy methyl)urea, 1-3-dimethyol-5,5-dimethyl hydantoin, iodopropynyl butyl carbamate, butyl paraben, ethyl paraben, methyl paraben, propyl paraben, methyl isothiazolinone, methyl-chloroisothiazoline, phenoxyethanol, tris-hydroxy-ethyl-hexahydrotriazine, methylisothiazolinone, 5-chloro-2-methyl-4-isothiazolin-3-one, 1,2-dibromo-2,4-dicyanobutane, 1-(3-chloroalkyl)-3,5,7-triaza-azoniaadamantane chloride, organic acids, or combinations thereof.

27. The personal care composition of claim 23, wherein the personal care composition is a face wash composition, and optionally further comprises one or more of:
a zinc salt skin flora regulator active;
a humectant selected from glycerin, lactic acid, propylene glycol, sodium PCA, sorbitol, and mixtures thereof; and
a conditioner.

28. The shower gel composition of claim 21, further comprising caprylyl glycol active.

29. The face wash composition of claim 27, further comprising one or more optional ingredients selected from fragrances, vitamins, extracts, proteins, antioxidants, pearlizers, opacifiers and a combination of two or more thereof.

30. The composition of claim 23, comprising added water in an amount of from 65% to 75% by weight of the composition.

31. A method of cleansing skin comprising applying to the skin a composition according to claim 21.

* * * * *